United States Patent
Song

(10) Patent No.: US 9,200,749 B2
(45) Date of Patent: Dec. 1, 2015

(54) ULTRASONIC DIAGNOSTIC APPARATUS WITH HEIGHT ADJUSTING DEVICE OF CONTROL PANEL

(71) Applicant: SAMSUNG MEDISON CO., LTD., Gangwon-do (KR)

(72) Inventor: Jung Sik Song, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 143 days.

(21) Appl. No.: 13/733,686

(22) Filed: Jan. 3, 2013

(65) Prior Publication Data

US 2013/0168511 A1 Jul. 4, 2013

(30) Foreign Application Priority Data

Jan. 3, 2012 (KR) .................. 10-2012-0000606

(51) Int. Cl.
*F16M 13/02* (2006.01)
*F16H 37/02* (2006.01)
*F16M 11/18* (2006.01)
*F16M 11/20* (2006.01)
*F16M 11/24* (2006.01)
*F16M 11/42* (2006.01)
*A61B 8/00* (2006.01)

(52) U.S. Cl.
CPC ............ *F16M 13/022* (2013.01); *A61B 8/4405* (2013.01); *F16H 37/02* (2013.01); *F16M 11/18* (2013.01); *F16M 11/2092* (2013.01); *F16M 11/24* (2013.01); *F16M 11/42* (2013.01); *A61B 8/462* (2013.01); *A61B 8/56* (2013.01); *F16M 2200/044* (2013.01); *F16M 2200/063* (2013.01); *Y10T 74/18568* (2015.01)

(58) Field of Classification Search
CPC ..... F16M 13/022; F16M 11/04; F16M 11/18; F16M 2200/063; F16D 7/044; F16D 11/10; F16D 11/14
USPC ............ 600/437; 248/125.2, 188.2, 655, 669, 248/404, 276.1, 281.11, 284.1; 192/99 S, 192/48.5, 69.82–69.83, 89.27; 74/405
See application file for complete search history.

(56) References Cited

U.S. PATENT DOCUMENTS

| | | | | |
|---|---|---|---|---|
| 1,250,687 A * | 12/1917 | Smith | .......................... | 192/53.5 |
| 1,907,619 A * | 5/1933 | Soden-Fraunhofen | .... | 192/69.83 |
| 2,541,885 A * | 2/1951 | Neely | ................................ | 57/79 |
| 2,658,396 A * | 11/1953 | Christiance | ....................... | 74/96 |
| 3,934,688 A * | 1/1976 | Sides et al. | ..................... | 192/48.5 |
| 4,474,218 A * | 10/1984 | Sample | ......................... | 139/1 E |
| 5,129,397 A * | 7/1992 | Jingu et al. | .................... | 600/437 |
| 5,333,712 A * | 8/1994 | Sabee et al. | ................... | 192/56.2 |

(Continued)

*Primary Examiner* — Ingrid M Weinhold
(74) *Attorney, Agent, or Firm* — McDermott Will & Emery LLP

(57) ABSTRACT

An ultrasonic diagnostic apparatus including a body, a control panel installed on the top of the body, and a height adjusting device to adjust a height of the control panel. The height adjusting device includes an installation bracket for installation of constituent elements of the height adjusting device, a drive motor to generate rotational power, and at least one arm having one end rotatably coupled to the installation bracket and another end rotatably coupled to the control panel. A clutch unit is placed operationally between the drive motor and the arm to selectively cutoff power transmission between the drive motor and the arm. Thus, the height of the control panel is manually adjustable after the clutch unit cuts off power transmission between the drive motor and the arm.

13 Claims, 6 Drawing Sheets

(56) References Cited

U.S. PATENT DOCUMENTS

| | | | |
|---|---|---|---|
| 5,698,073 A * | 12/1997 | Vincenzi | 160/188 |
| 5,713,549 A * | 2/1998 | Shieh | 248/284.1 |
| 6,651,793 B2 * | 11/2003 | Reisinger | 192/35 |
| 6,663,569 B1 * | 12/2003 | Wilkins et al. | 600/459 |
| 8,366,097 B2 * | 2/2013 | Tu et al. | 271/10.13 |
| 8,758,246 B2 * | 6/2014 | Song | 600/437 |
| 2003/0220564 A1 * | 11/2003 | Wilkins et al. | 600/437 |
| 2010/0006727 A1 * | 1/2010 | Boomgaarden et al. | 248/276.1 |

* cited by examiner

ULTRASONIC DIAGNOSTIC APPARATUS WITH HEIGHT ADJUSTING DEVICE OF CONTROL PANEL

CROSS-REFERENCE TO RELATED APPLICATION

This application claims the benefit of Korean Patent Application No. 10-2012-0000606, filed on Jan. 3, 2012 in the Korean Intellectual Property Office, the disclosure of which is incorporated herein by reference.

BACKGROUND

1. Field

Exemplary embodiments of the present disclosure relate to an ultrasonic diagnostic apparatus having a height adjusting device to adjust the height of a control panel.

2. Description of the Related Art

Generally, an ultrasonic diagnostic apparatus is an apparatus that irradiates ultrasonic waves to, for example, the surface of the body of a person (hereinafter referred to as an "object") at an internal body region to be diagnosed, and acquires tomography of soft tissues or images of blood flow via the reflected ultrasonic waves.

An ultrasonic diagnostic apparatus includes a body, a probe that transmits ultrasonic signals to an object and receives the ultrasonic signals reflected from the object, a display unit that is installed above the body to display images showing diagnostic results acquired by the received ultrasonic signals, and a control panel that is placed in front of the display unit for assisting a user in operating the ultrasonic diagnostic apparatus.

In the above-described ultrasonic diagnostic apparatus, the control panel is provided with a height adjusting device to assist the user in adjusting the height of the control panel to accommodate physical attributes of the user and to adapt to various environments in which the ultrasonic diagnostic apparatus may be used.

The height adjusting device includes an arm having one end rotatably coupled to the body and another end coupled to the control panel. The height of the control panel is adjusted by rotating the arm.

The height adjusting device may be of an automatic type in which the height of the control panel is adjusted using power generated from, e.g., a drive motor, or may be of a manual type in which the height of the control panel is adjusted directly by user manipulation.

SUMMARY

It is an object of the present disclosure to provide an improved ultrasonic diagnostic apparatus in which the height of a control panel is adjustable automatically or manually.

Additional objects of the present disclosure will be set forth in part in the description which follows and, in part, will be obvious from the description, or may be learned by practice of exemplary embodiments of the present disclosure.

In accordance with one aspect of the present disclosure, an ultrasonic diagnostic apparatus includes a body, a control panel installed on the body, and a height adjusting device to adjust a height of the control panel, wherein the height adjusting device includes an installation bracket coupled to the body, a drive motor to generate rotational power, at least one arm having one end rotatably coupled to the installation bracket and another end rotatably coupled to the control panel, and a clutch unit placed operationally between the drive motor and the at least one arm to selectively cutoff power transmission between the drive motor and the at least one arm.

The clutch unit may include a driving gear adapted to be rotated upon receiving rotational power from the drive motor, a driven gear to transmit rotational power to the at least one arm, a power-transmission shaft having one end to which the driving gear is secured, and another end to which the driven gear is rotatably coupled, and a moving coupler arranged on the power-transmission shaft so as to be movable in an axial direction of the power-transmission shaft and rotatable with the power-transmission shaft, the moving coupler being movable from a first position where the moving coupler is engaged with the driven gear to a second position where the moving coupler is spaced apart from the driven gear.

The power-transmission shaft may include a first surface-treated portion formed at one end thereof to which the driving gear is secured, and a second surface-treated portion, formed at a middle portion thereof, to which the moving coupler is movably coupled, the driving gear may have a center shaft fixing hole having a shape corresponding to the first surface-treated portion, and the moving coupler may have a center guide hole having a shape corresponding to the second surface-treated portion.

The driven gear may include a shaft installation hole into which the power-transmission shaft is rotatably fitted, and a first coupling portion formed at a surface thereof facing the moving coupler, and the moving coupler may have a second coupling portion formed at a surface thereof facing the driven gear, the second coupling portion being engaged with the first coupling portion in the first position.

The first coupling portion may include ridges and valleys alternately formed circumferentially around the shaft installation hole, and the second coupling portion may include ridges and valleys alternately formed circumferentially around the center guide hole.

The clutch unit may further include a first elastic member having one end supported by the driving gear and another end supported by the moving coupler, the first elastic member biasing the moving coupler into the first position.

The clutch unit may further include a second elastic member having one end supported by the driven gear and another end supported by the moving coupler, the second elastic member having less elasticity than that of the first elastic member.

The clutch unit may further include a lever to transmit force to the moving coupler, the moving coupler may include a radially extending flange portion to receive force transmitted from the lever, and the lever may include a lever portion formed at one end thereof to which force is applied by a user, a pressure portion formed at another end thereof to apply force to the flange portion, and a pressure roller rotatably provided at a tip end of the pressure portion.

The arm may include a gear portion extending from one end thereof to have a fan shape, and the gear portion may have gear teeth formed at an outer peripheral surface thereof so as to be engaged with the driven gear.

In accordance with another aspect of the present disclosure, a height adjusting device for adjusting a height of a control panel includes an installation bracket, a drive motor to generate rotational power, at least one arm having one end rotatably coupled to the installation bracket and another end adapted to be rotatably coupled to the control panel, and a clutch unit placed operationally between the drive motor and the at least one arm to selectively cutoff power transmission between the drive motor and the at least one arm.

The clutch unit may include a lever configured to be selectively moved between a first position in which the drive motor supplies rotational power to the at least one arm and a second position in which the drive motor does not supply rotational power to the at least one arm.

The clutch unit may further include an elastic member biasing the lever into the first position.

The clutch unit may be arranged and configured such that in a first position the clutch unit transmits rotational power from the drive motor to the at least one arm and in a second position the clutch unit disconnects rotational power from the drive motor to the at least one arm.

The at least one arm may be configured to be manually rotatable independent of the drive motor when the clutch unit is in the second position.

BRIEF DESCRIPTION OF THE DRAWINGS

These and/or other aspects of the present disclosure will become apparent and more readily appreciated from the following description of exemplary embodiments, taken in conjunction with the accompanying drawings of which.

DETAILED DESCRIPTION

Figure 1:
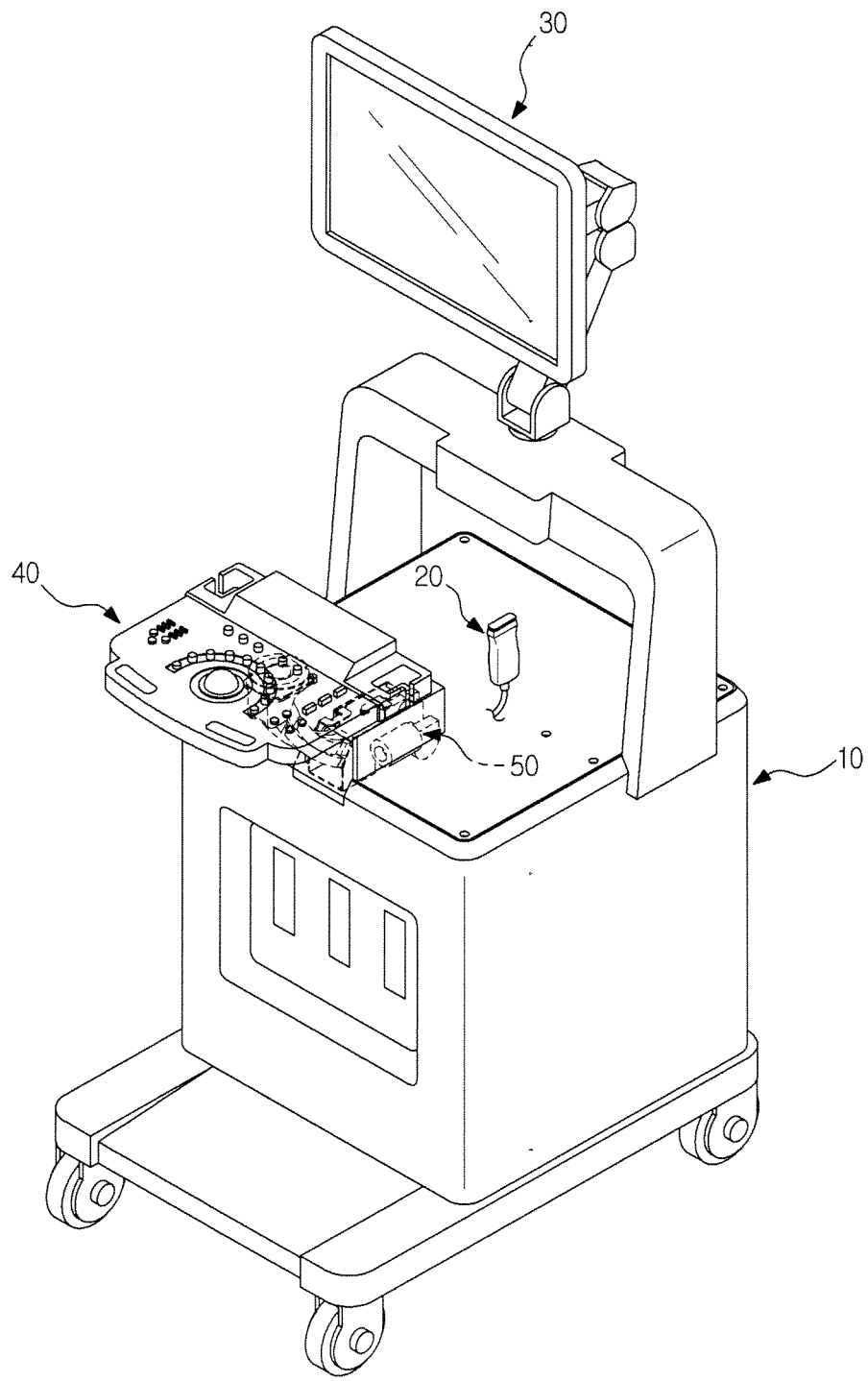
FIG. 1 is a perspective view of an ultrasonic diagnostic apparatus according to an exemplary embodiment of the present disclosure.

Reference will now be made in detail to an ultrasonic diagnostic apparatus according to an exemplary embodiment of the present disclosure, examples of which are illustrated in the accompanying drawings, wherein like reference numerals refer to like elements throughout.

The ultrasonic diagnostic apparatus according to an exemplary embodiment of the present disclosure, as illustrated in FIG. 1, includes a body 10, a probe 20 that transmits ultrasonic signals to an object to be diagnosed and receives the ultrasonic signals reflected from the object, a display unit 30 coupled to the body 10 to display images showing diagnostic results acquired by the received ultrasonic waves, and a control panel 40 for assisting a user in operating the ultrasonic diagnostic apparatus.

The ultrasonic diagnostic apparatus includes a height adjusting device 50 to assist the user in adjusting the height of the control panel 40 to accommodate physical attributes of the user and to adapt to various environments in which the ultrasonic diagnostic apparatus may be used.

Figure 2:
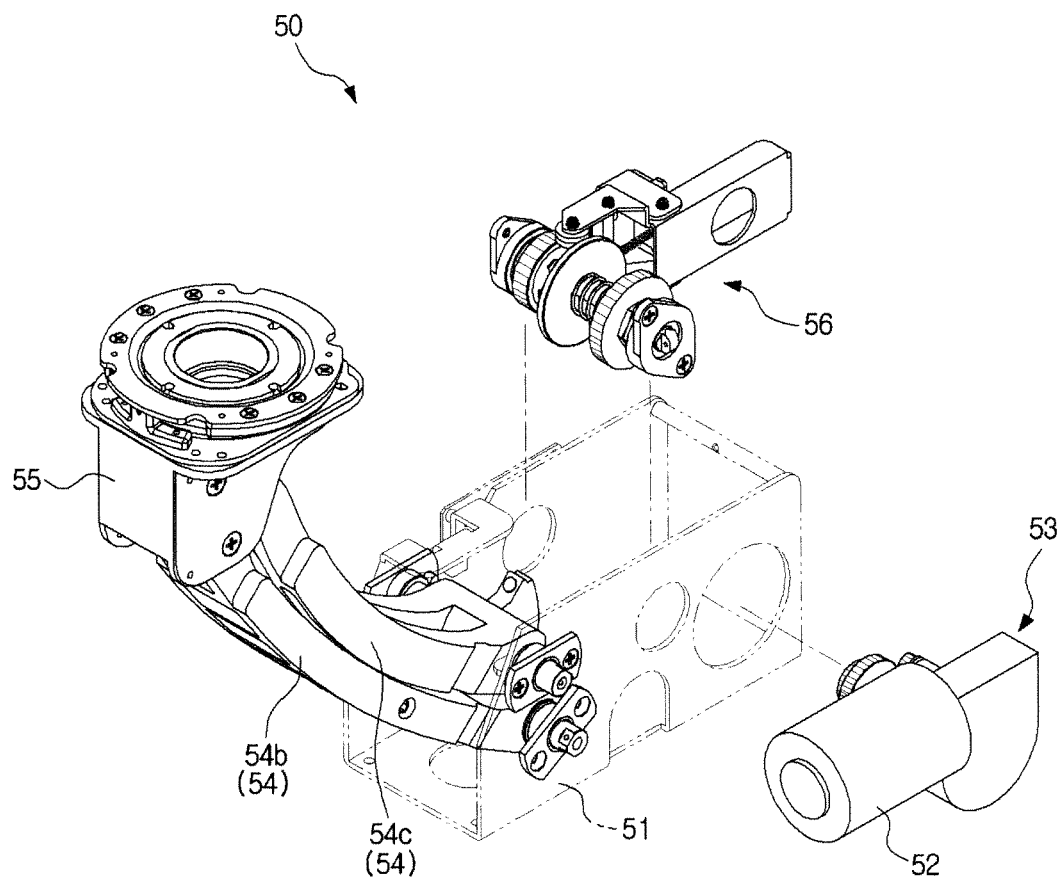
FIG. 2 is an exploded perspective view of a height adjusting device included in the ultrasonic diagnostic apparatus according to an exemplary embodiment of the present disclosure.

As shown in FIG. 2, the height adjusting device 50 includes an installation bracket 51 secured to the body 10 for installation of constituent elements of the height adjusting device 50, a drive motor 52 to generate rotational power, a speed-reduction unit 53 including a plurality of gears for speed reduction, an arm 54 having one end rotatably coupled to the installation bracket 51 and another end rotatably coupled to the control panel 40, and a rotatable bracket 55 secured to a lower surface of the control panel 40 so as to be rotatable clockwise or counterclockwise, the another end of the arm 54 being coupled to the rotatable bracket 55 so as to be pivotally rotatable upward or downward. In the present exemplary embodiment, the arm 54 includes a pair of arms 54b and 54c arranged one above another, the pair of arms 54b and 54c serving to assist the control panel 40 in moving upward or downward while maintaining an upper surface of the control panel 40 facing upward.

Figure 3:
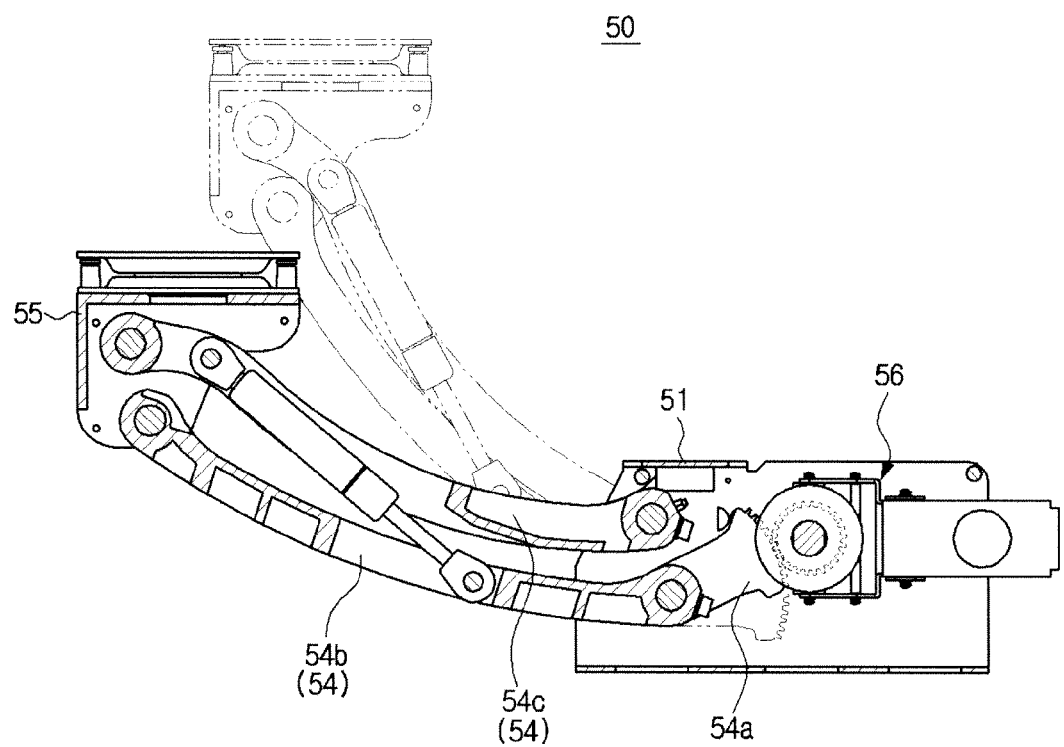
FIG. 3 is a side view illustrating an operation of the height adjusting device included in the ultrasonic diagnostic apparatus according to an exemplary embodiment of the present disclosure.

Accordingly, if the user operates buttons, etc., provided on the control panel 40, rotational power generated by the drive motor 52 is transmitted to at least one of the pair of arms 54. Thereby, the arm 54, as illustrated in FIG. 3, can be rotated about the one end thereof, causing the control panel 40 coupled to the another end of the arm 54 to move upward (shown in dotted lines) or downward.

In the above-described height adjusting device 50, the arm 54 is adapted to be rotated by power transmitted from the drive motor 52. With this configuration, if the user attempts to manually adjust the height of the control panel 40 by applying force to the control panel 40, it may be necessary for the user to apply sufficient force to the control panel 40 to rotate all of the gears of the speed-reduction unit 53 and a rotating shaft of the drive motor 52. Therefore, manually adjusting the control panel 40 may require that the user applies a relatively large amount of force to the control panel 40. However, it may be impossible to manually adjust the height of the control panel 40 if the speed-reduction unit 53 includes a gear that permits power transmission only in a given direction.

Accordingly, the height adjusting device 50 included in the ultrasonic diagnostic apparatus according to the present exemplary embodiment includes a clutch unit 56 to assist the user in manually adjusting the height of the control panel 40.

The clutch unit 56 is placed operationally between the drive motor 52 and the arm 54 and serves to cutoff power transmission between the drive motor 52 and the arm 54. This allows the arm 54 to be rotated independent of the drive motor 52 or the speed-reduction unit 53 by disconnecting transmission of power between the drive motor 52 and the arm 54 when the user attempts to manually adjust the height of the control panel 40.

Figure 4:
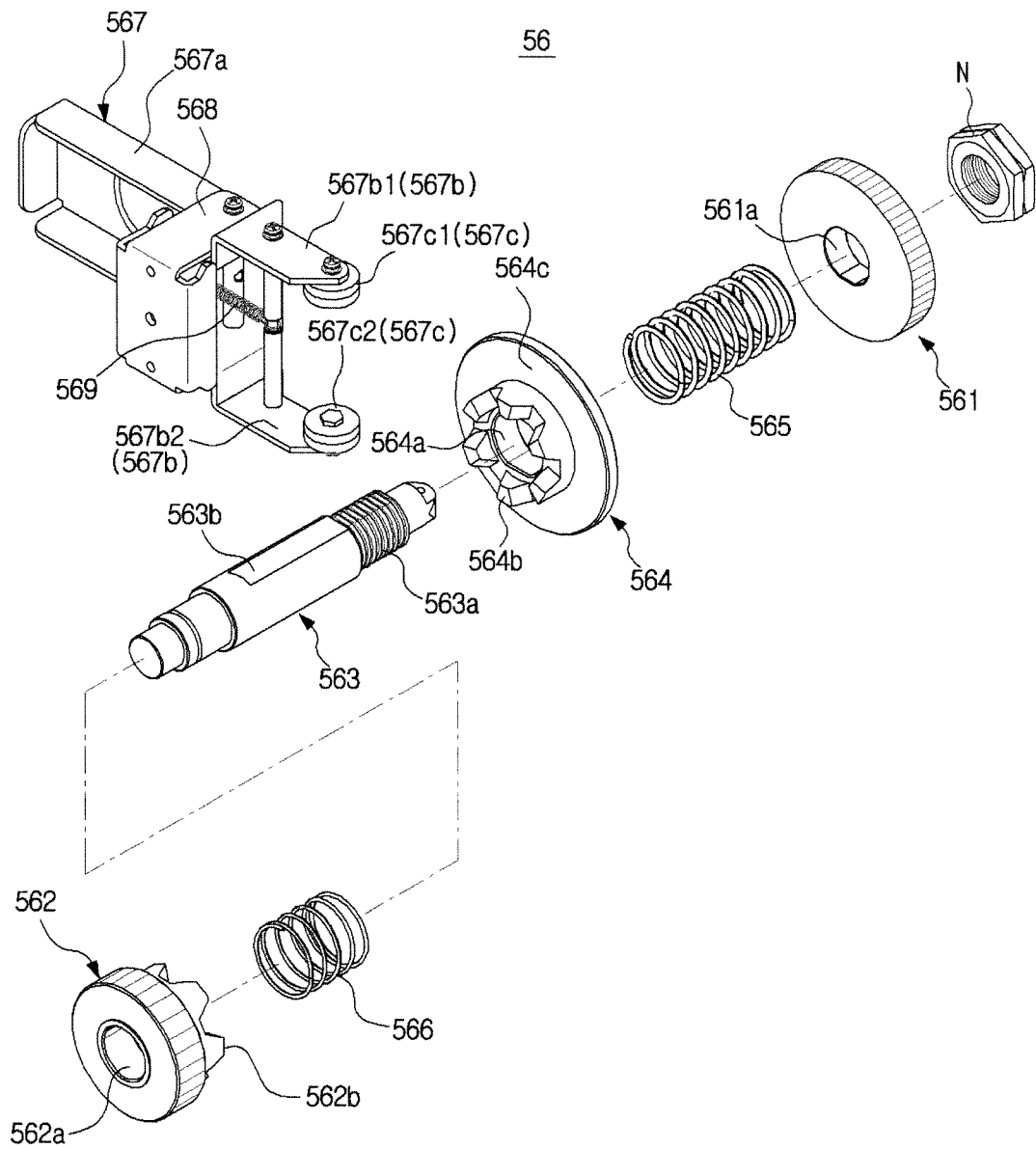
FIG. 4 is an exploded perspective view of a clutch unit included in the ultrasonic diagnostic apparatus according to an exemplary embodiment of the present disclosure.

The clutch unit 56, as illustrated in FIG. 4, includes a driving gear 561 that is rotated upon receiving power from the drive motor 52 via the speed-reduction unit 53, a driven gear 562 that transmits rotational power to the arm 54, a power-transmission shaft 563 that has one end to which the driving gear 561 is fastened and another end to which the driven gear 562 is rotatably coupled, and a moving coupler 564 that is arranged on the power-transmission shaft 563 so as to be movable in an axial direction of the power-transmission shaft 563. The moving coupler 564 is adapted to move between a first position where the moving coupler 564 is coupled to the driven gear 562 and a second position where the moving coupler 564 is spaced apart from the driven gear 562.

The arm 54 is rotated upon receiving rotational power from the driven gear 562. To this end, the arm 54 is provided at one end thereof with a gear portion 54a. The gear portion 54a extends in a fan shape and has gear-teeth formed at an outer peripheral surface thereof (FIG. 3) so as to be engaged with the driven gear 562.

The driving gear 561 and the moving coupler 564 are rotated along with the power-transmission shaft 563. To this end, the power-transmission shaft 563 is provided at one end thereof with a first surface-treated portion 563a, to which the driving gear 561 is fastened. The driving gear 561 has a center shaft fixing hole 561a having a shape corresponding to the first surface-treated portion 563a. A male screw thread is formed on the first surface-treated portion 563a for fastening a nut N that is used to fix the driving gear 561 to the power-transmission shaft 563. The power-transmission shaft 563 has a second surface-treated portion 563b to allow the moving coupler 564 to be movably coupled to the power-transmission shaft 563. The moving coupler 564 has a center guide hole 564a having a shape corresponding to the second surface-treated portion 563b.

The driven gear 562 has a center shaft installation hole 562a, into which the above-described power-transmission shaft 563 is rotatably fitted. According to this configuration, the driven gear 562 does not receive rotational power directly from the power-transmission shaft 563, but rather, is rotated upon receiving rotational power through the moving coupler 564 coupled to the power-transmission shaft 563.

The driven gear 562 has a first coupling portion 562b formed on a surface thereof facing the moving coupler 564 to receive rotational power from the moving coupler 564. The moving coupler 564 has a second coupling portion 564b formed on a surface thereof facing the driven gear 562 so as to be engaged with the first coupling portion 562b. The first coupling portion 562b has ridges and valleys alternately formed circumferentially around the center shaft installation hole 562a of the driven gear 562. The second coupling portion 564b has ridges and valleys alternately formed circumferentially around the center guide hole 564a.

In the case of automatically adjusting the height of the control panel 40, the moving coupler 564 is coupled to the driven gear 562. To this end, the clutch unit 56 includes a first elastic member 565 in the form of, for example, a coil spring. The first elastic member 565 is inserted on the power-transmission shaft 563 such that one end thereof is supported by the driving gear 561 and another end thereof is supported by the moving coupler 564.

The clutch unit 56 further includes a second elastic member 566 in the form of, for example, a coil spring, to assist movement of the moving coupler 564. The second elastic member 566 is inserted on the power-transmission shaft 563 such that one end thereof is supported by the driven gear 562 and another end thereof is supported by the moving coupler 564. In this case, since an engagement between the moving coupler 564 and the driven gear 562 may need to be maintained before an external force is applied to the moving coupler 564, the second elastic member 566 has less elasticity than that of the first elastic member 565.

The clutch unit 56 further includes a lever 567 to move the moving coupler 564 by applying external force to the moving coupler 564, a hinge member 568 to assist the lever 567 in being rotatably installed in the installation bracket 51, and a third elastic member 569 having one end coupled to the lever 567 and another end coupled to the hinge member 568.

The lever 567 includes a lever portion 567a formed at one end thereof to protrude outward from the installation bracket 51 such that the user can apply force thereto, and a pressure portion 567b formed at another end thereof to apply force to the moving coupler 564. The moving coupler 564 includes a radially extending flange portion 564c arranged and configured to receive force applied from the pressure portion 567b. The third elastic member 569 elastically supports the lever 567 to assist the pressure portion 567b of the lever 567 in remaining spaced apart from the flange portion 564c when no force is applied to the lever 567.

In the present exemplary embodiment, the pressure portion 567b includes a pair of pressure portions 567b1 and 567b2 to apply pressure to both sides of the flange portion 564c to ensure stable movement of the moving coupler 564. A pressure roller 567c includes rollers 567c1 and 567c2 which are arranged respectively at tip ends of the pressure portions 567b1 and 567b2 to come into rolling contact with the flange portion 564c.

Figure 5:
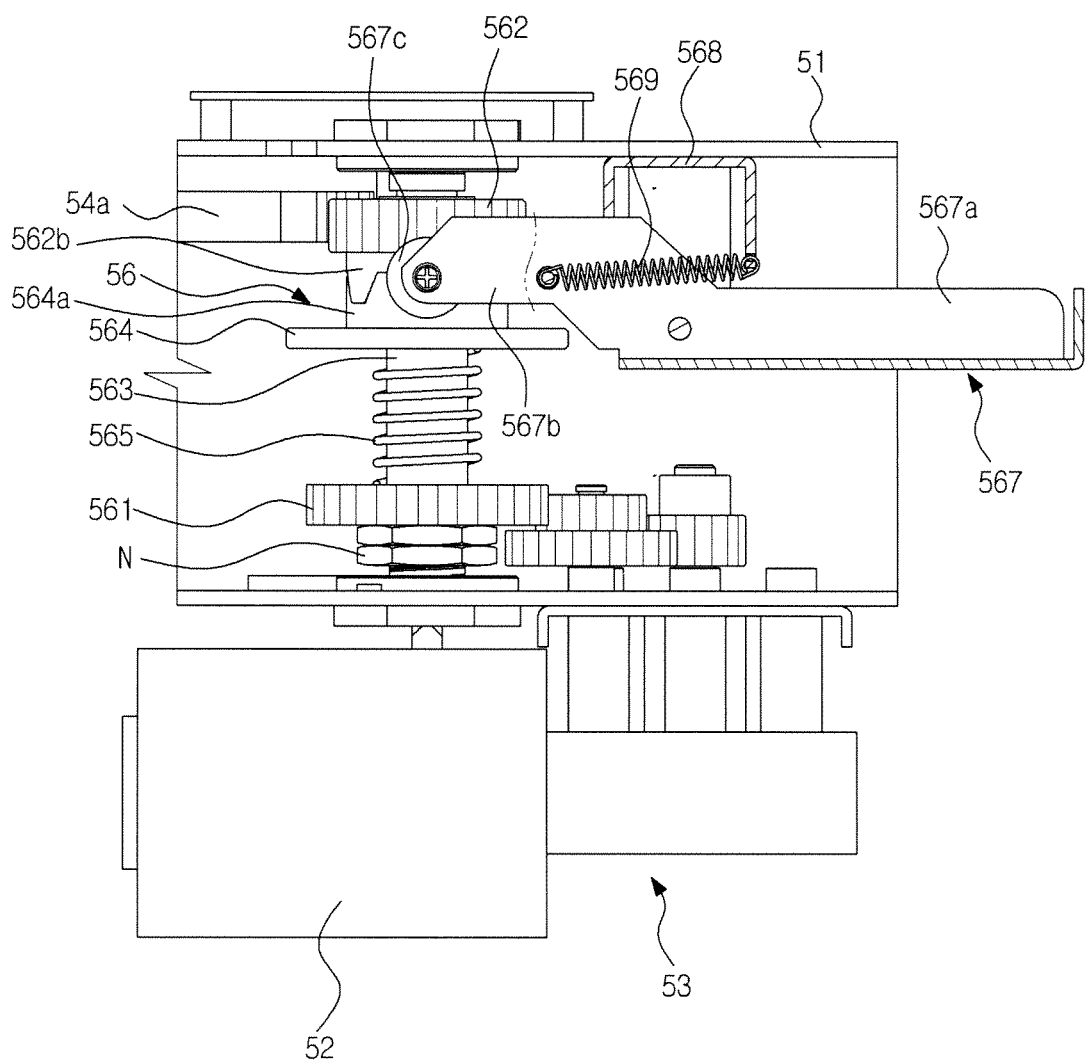
FIGS. 5 and 6 are plan views illustrating an operation of the clutch unit included in the ultrasonic diagnostic apparatus's according to an exemplary embodiment of the present disclosure.

Accordingly, when the height of the control panel 40 is adjusted automatically, as illustrated in FIG. 5, the first coupling portion 562b of the driven gear 562 and the second coupling portion 564b of the moving coupler 564 are engaged with each other by elasticity of the first elastic member 565, which ensures transmission of rotational power from the power-transmission shaft 563 to the driven gear 562.

Figure 6:
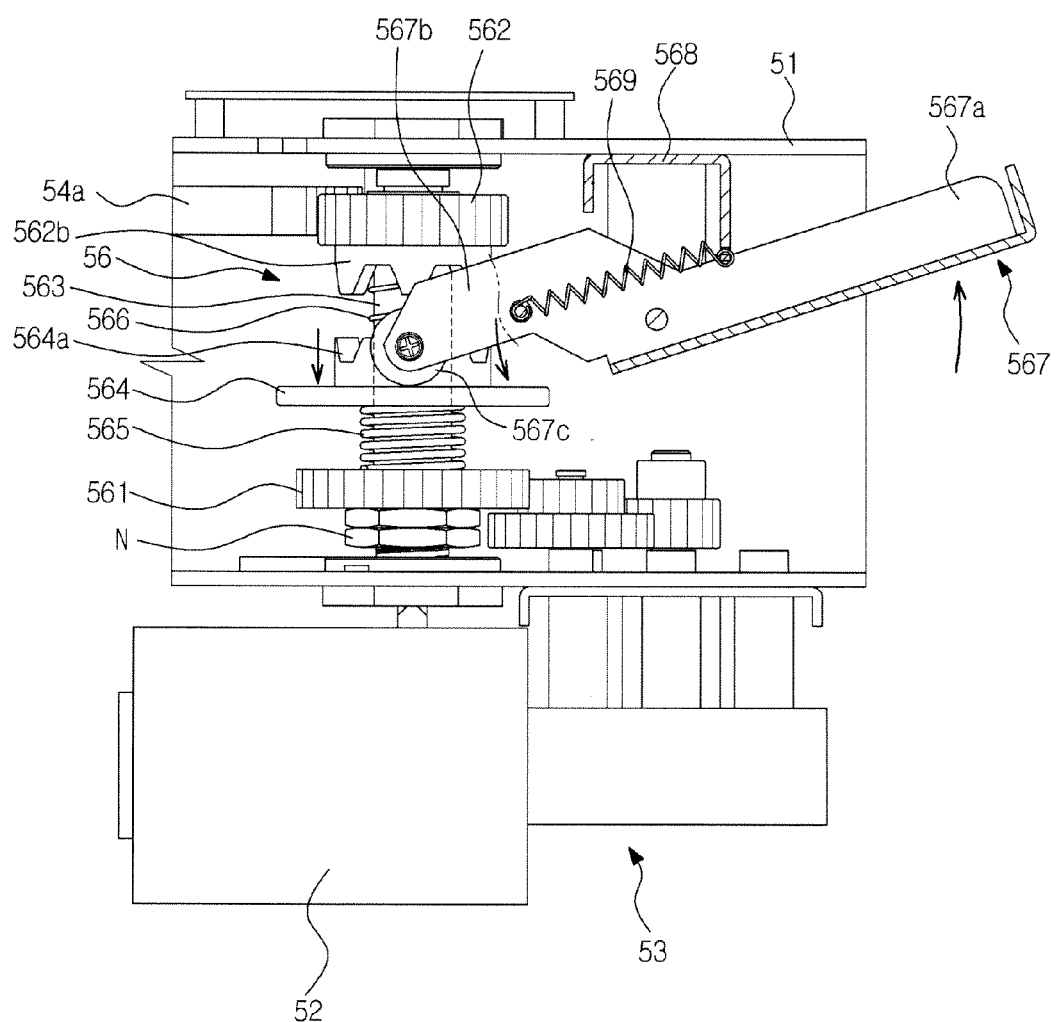

When the user wants to manually adjust the height of the control panel 40 via, for example, power cutoff, as illustrated in FIG. 6, if the user applies force to the lever portion 567a of the lever 567, the lever 567 is rotated such that the pressure roller 567c provided at the tip end of the pressure portion 567b of the lever 567 comes into contact with the flange portion 564c, thereby transmitting force to the flange portion 564c. As the first elastic member 565 is elastically deformed by external force transmitted to the flange portion 564c, the moving coupler 564 is moved from a first position where the moving coupler 564 is coupled to the driven gear 562 to a second position where the moving coupler 564 is spaced apart from the driven gear 562. Thereby, the first coupling portion 562b and the second coupling portion 564b, which have been engaged with each other, are moved away from each other, which cuts off power-transmission between the driven gear 562 and the moving coupler 564.

Then, if the user applies force to the control panel 40, the arm 54 and the driven gear 562 connected to the gear portion 54a of the arm 54 are rotated by the force applied by the user. However, since the driven gear 562 is spaced apart from the moving coupler 564 as described above, the force is not transmitted to the power-transmission shaft 563. That is, the user may adjust the height of the control panel 40 by applying a relatively small force required to rotate only the arm 54 and the driven gear 562.

As is apparent from the above description, according to examples embodied by the present disclosure, a height adjusting device usable with an ultrasonic diagnostic apparatus includes a clutch unit to cutoff transmission of power between a drive motor and an arm. Once the clutch unit cuts off transmission of power between the drive motor and the arm, the height of a control panel may be easily adjusted manually.

Although exemplary embodiments of the present disclosure have been shown and described, it would be appreciated by those having ordinary skill in the art that changes may be made in these embodiments without departing from the principles and spirit of the disclosure, the scope of which is defined in the claims and their equivalents.

What is claimed is:

1. An ultrasonic diagnostic apparatus with a height adjusting device of a control panel comprising:
   a body;
   the control panel installed on the body; and
   the height adjusting device adjusting a height of the control panel, the height adjusting device including:
   an installation bracket coupled to the body;
   a drive motor generating a rotational power;
   at least one arm having one end rotatably coupled to the installation bracket and another end rotatably coupled to the control panel; and
   a clutch unit disposed operationally between the drive motor and the at least one arm to selectively cutoff power transmission between the drive motor and the at least one arm, wherein the clutch unit includes:
a driving gear rotating upon receiving the rotational power from the drive motor;
a driven gear transmitting the rotational power to the at least one arm;
a power-transmission shaft having one end to which the driving gear is secured, and another end to which the driven gear is rotatably coupled;
a moving coupler arranged on the power-transmission shaft to be movable in an axial direction of the power-transmission shaft and rotatable with the power-transmission shaft, the moving coupler being movable from a first position where the moving coupler is engaged with the driven gear to a second position where the moving coupler is spaced apart from the driven gear;
a first elastic member having one end supported by the driving gear and another end supported by the moving coupler; and
a second elastic member having one end supported by the moving coupler, and
wherein the power-transmission shaft includes a first surface-treated portion formed at one end of the power-transmission shaft to which the driving gear is secured, and a second surface-treated portion formed at a middle portion of the power-transmission shaft such that the moving coupler is movably coupled to the power-transmission shaft, and
wherein the second elastic member has an elasticity smaller than that of the first elastic member.

2. The apparatus according to claim 1,
wherein the driving gear has a center shaft fixing hole having a shape corresponding to the first surface-treated portion, and
wherein the moving coupler has a center guide hole having a shape corresponding to the second surface-treated portion.

3. The apparatus according to claim 2,
wherein the driven gear includes a shaft installation hole into which the power-transmission shaft is rotatably fitted, and a first coupling portion formed at a surface thereof facing the moving coupler, and
wherein the moving coupler has a second coupling portion formed at a surface thereof facing the driven gear, the second coupling portion being engaged with the first coupling portion in the first position.

4. The apparatus according to claim 3,
wherein the first coupling portion includes ridges and valleys alternately formed circumferentially around the shaft installation hole, and
wherein the second coupling portion includes ridges and valleys alternately formed circumferentially around the center guide hole.

5. The apparatus according to claim 1, wherein the first elastic member biases the moving coupler into the first position.

6. The apparatus according to claim 1,
wherein the clutch unit further includes a lever to transmit a force to the moving coupler,
wherein the moving coupler includes a radially extending flange portion to receive the force transmitted from the lever, and
wherein the lever includes a lever portion formed at one end thereof to which the force is applied by a user, a pressure portion formed at another end thereof to apply the force to the flange portion, and a pressure roller rotatably provided at a tip end of the pressure portion.

7. The apparatus according to claim 1, wherein the at least one arm includes a gear portion extending from one end thereof, and the gear portion has gear teeth formed at an outer peripheral surface thereof to be engaged with the driven gear.

8. A height adjusting device for adjusting a height of a control panel, the height adjusting device comprising:
an installation bracket;
a drive motor generating a rotational power;
at least one arm having one end rotatably coupled to the installation bracket and another end rotatably coupled to the control panel; and
a clutch unit disposed operationally between the drive motor and the at least one arm to selectively cutoff power transmission between the drive motor and the at least one arm,
wherein the clutch unit includes:
a driving gear rotating upon receiving the rotational power from the drive motor;
a driven gear transmitting the rotational power to the at least one arm;
a power-transmission shaft having one end to which the driving gear is secured, and another end to which the driven gear is rotatably coupled;
a moving coupler arranged on the power-transmission shaft to be movable in an axial direction of the power-transmission shaft and rotatable with the power-transmission shaft, the moving coupler being movable from a first position where the moving coupler is engaged with the driven gear to a second position where the moving coupler is spaced apart from the driven gear;
a first elastic member having one end supported by the driving gear and another end supported by the moving coupler; and
a second elastic member having one end supported by the moving coupler, and
wherein the power-transmission shaft includes a first surface-treated portion formed at one end of the power-transmission shaft to which the driving gear is secured, and a second surface-treated portion formed at a middle portion of the power-transmission shaft such that the moving coupler is movably coupled to the power-transmission shaft, and
wherein the second elastic member has an elasticity smaller than that of the first elastic member.

9. The height adjusting device according to claim 8, wherein the clutch unit further includes a lever configured to selectively move between the first position in which the drive motor supplies the rotational power to the at least one arm and the second position in which the drive motor does not supply the rotational power to the at least one arm.

10. The height adjusting device according to claim 9, wherein the first elastic member biases the lever into the first position.

11. The height adjusting device according to claim 8, wherein the clutch unit is arranged and configured such that the clutch unit transmits the rotational power from the drive motor to the at least one arm in the first position and disconnects the rotational power from the drive motor to the at least one arm in the second position.

12. The height adjusting device according to claim 11, wherein the at least one arm is configured to be manually rotatable independent of the drive motor when the clutch unit is in the second position.

13. A height adjusting device for adjusting a height of a control panel, the height adjusting device comprising:
   an installation bracket;
   a drive motor generating a rotational power;
   at least one arm having one end movably coupled to the installation bracket and another end movably coupled to the control panel; and
   a clutch unit disposed operationally between the drive motor and the at least one arm to selectively cutoff power transmission between the drive motor and the at least one arm,
   wherein the clutch unit includes:
      a driving gear rotating upon receiving a rotational power from the drive motor;
      a driven gear transmitting the rotational power to the at least one arm;
      a power-transmission shaft having one end to which the driving gear is secured, and another end to which the driven gear is rotatably coupled;
      a moving coupler arranged on the power-transmission shaft to be movable in an axial direction of the power-transmission shaft and rotatable with the power-transmission shaft, the moving coupler being movable from a first position where the moving coupler is engaged with the driven gear to a second position where the moving coupler is spaced apart from the driven gear;
      a first elastic member having one end supported by the driving gear and another end supported by the moving coupler; and
      a second elastic member having one end supported by the moving coupler, and
   wherein the power-transmission shaft includes a first surface-treated portion formed at one end of the power-transmission shaft to which the driving gear is secured, and a second surface-treated portion formed at a middle portion of the power-transmission shaft such that the moving coupler is movably coupled to the power-transmission shaft, and
   wherein the second elastic member has an elasticity smaller than that of the first elastic member.

* * * * *